United States Patent [19]

Anthony et al.

[11] Patent Number: 4,972,866

[45] Date of Patent: Nov. 27, 1990

[54] PURGE CONTROL MODULE

[75] Inventors: Michael M. Anthony, Gaithersburg; George E. Toth, Columbia, both of Md.

[73] Assignee: LT Industries, Rockville, Md.

[21] Appl. No.: 318,338

[22] Filed: Mar. 3, 1989

[51] Int. Cl.⁵ .............................................. G05D 7/06
[52] U.S. Cl. .................................. 137/110; 220/88 B
[58] Field of Search ................. 137/12, 110, 240, 554; 220/88 B

[56] References Cited

U.S. PATENT DOCUMENTS 3,474,823 10/1969 Finlayson ............................ 137/554
4,802,502 2/1989 Williams ........................ 137/554 X

*Primary Examiner*—Robert G. Nilson
*Attorney, Agent, or Firm*—Saidman, Sterne, Kessler & Goldstein

[57] ABSTRACT

A purge module is provided which provides gas to an enclosure at a first flow rate in order to purge the enclosure of harmful gases. After the pressure within the enclosure has reached a predetermined level, a sensor enables gas at a low pressure to be supplied to the enclosure after a predetermined time has passed. The purge module also enables power to be supplied to the device being purged at the same time the purge gas flow rate is changed.

11 Claims, 2 Drawing Sheets

PURGE CONTROL MODULE

BACKGROUND OF THE INVENTION

1. Field of the Invention

The invention relates generally to devices for purging equipment of harmful gases and, more particularly, to a device for purging harmful gases from electro-optical measurement equipment.

2. Background

Equipment used for measuring the constituents of samples, such as the type of device taught by U.S. Pat. No. 4,540,282 to Landa et al., is subject to stringent safety requirements. If such equipment is subject to a chemical process in which harmful gases are present, there is a likelihood of serious mishap such as explosion if such measurement equipment is not purged of the harmful gases. When equipment is used in plant processes in which dangerous chemicals are present, the equipment may be subject to safety requirements and standards which are set by the government.

In order to meet the stringent purge requirements, purge devices have been developed. These devices, in large part, have serious drawbacks, the most notable being their large size.

One of the objects to the present invention is to have a purge module which is conveniently sized and simple.

SUMMARY OF THE INVENTION

In accordance with the purposes of the present invention, as embodied and described herein, the present invention is a purge control module for ensuring the safety of an instrument in a hazardous environment.

The purge control module has a fluid inlet which supplies gas through a high pressure regulator which is located downstream from the fluid inlet. The fluid inlet also supplies gas to a low pressure regulator which is also downstream of the fluid inlet and is in parallel with the high pressure regulator. Downstream of the high pressure regulator is a first valve which has an open position and a closed position. When the first valve is in a closed position, a device for activating a switch is in fluid communication with the fluid passing through the high pressure regulator.

There is a second valve located downstream of the low pressure regulator. This second valve has a first position in which fluid passing through the second regulator passes through the valve and into an enclosure at a first flow rate. The second valve also has a second position in which fluid passing through the second regulator passes through the second valve at a second flow rate. The second position of the second valve is activated upon activation of the switch which is located downstream from the high pressure regulator.

A sensor determines whether the pressure within the enclosure has exceeded a predetermined level. If it has, power from a power source is supplied to the first valve and the valve moves from an open position to a closed position, thereby allowing fluid to be in communication with the device for activating the switch. In addition, which the switch is activated, power is supplied to the enclosure.

In one aspect of the invention, the device for activating the switch is a piston. When fluid impinges upon the piston, the piston moves down a cylinder to activate the switch. The motion of the piston is timed so that the enclosure has exchanged, for example, at least seven volumes of gas prior to the piston activating the switch.

In yet another aspect of the invention, a method of purging a module is provided. The method of purging a module includes the step of supplying an inert gas to an enclosure at a first flow rate. The second step is to sense when the pressure within the enclosure is greater than a predetermined pressure, the predetermined pressure being greater than ambient pressure. At this point, inert gas is supplied to the enclosure at a second flow rate which is lower than the flow rate originally supplied to the enclosure. The supplying of the inert gas to the enclosure at the slow flow rate occurs after a predetermined time. This predetermined time is long enough for harmful gases to be purged from an enclosure. Finally, power is supplied to the enclosure at the same predetermined time after the pressure has been determined to the greater than the predetermined pressure.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE PREFERRED EMBODIMENT

The present invention comprises a purge control module. This module is intended to provide a device for ensuring the safety of an instrument in a hazardous environment by purging harmful gases from equipment which has been subjected to dangerous and harmful chemical processes.

The module mounts directly onto an instrument enclosure and is attached thereto in any conventional manner. Preferably, there is a gasket or other means to prevent gas leaks between the module and the instrument enclosure.

Figure 1:
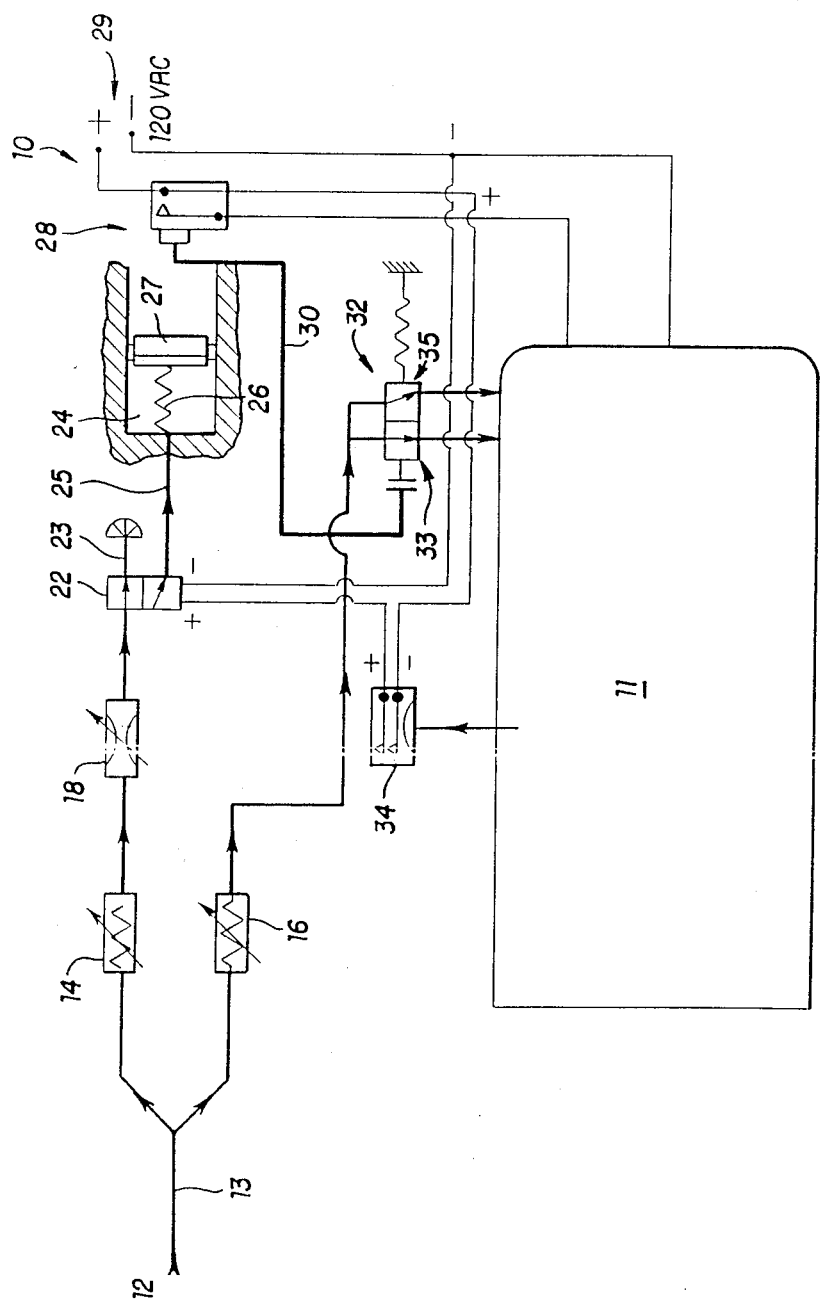
FIG. 1 is a schematic representation of the present invention.
Figure 2:
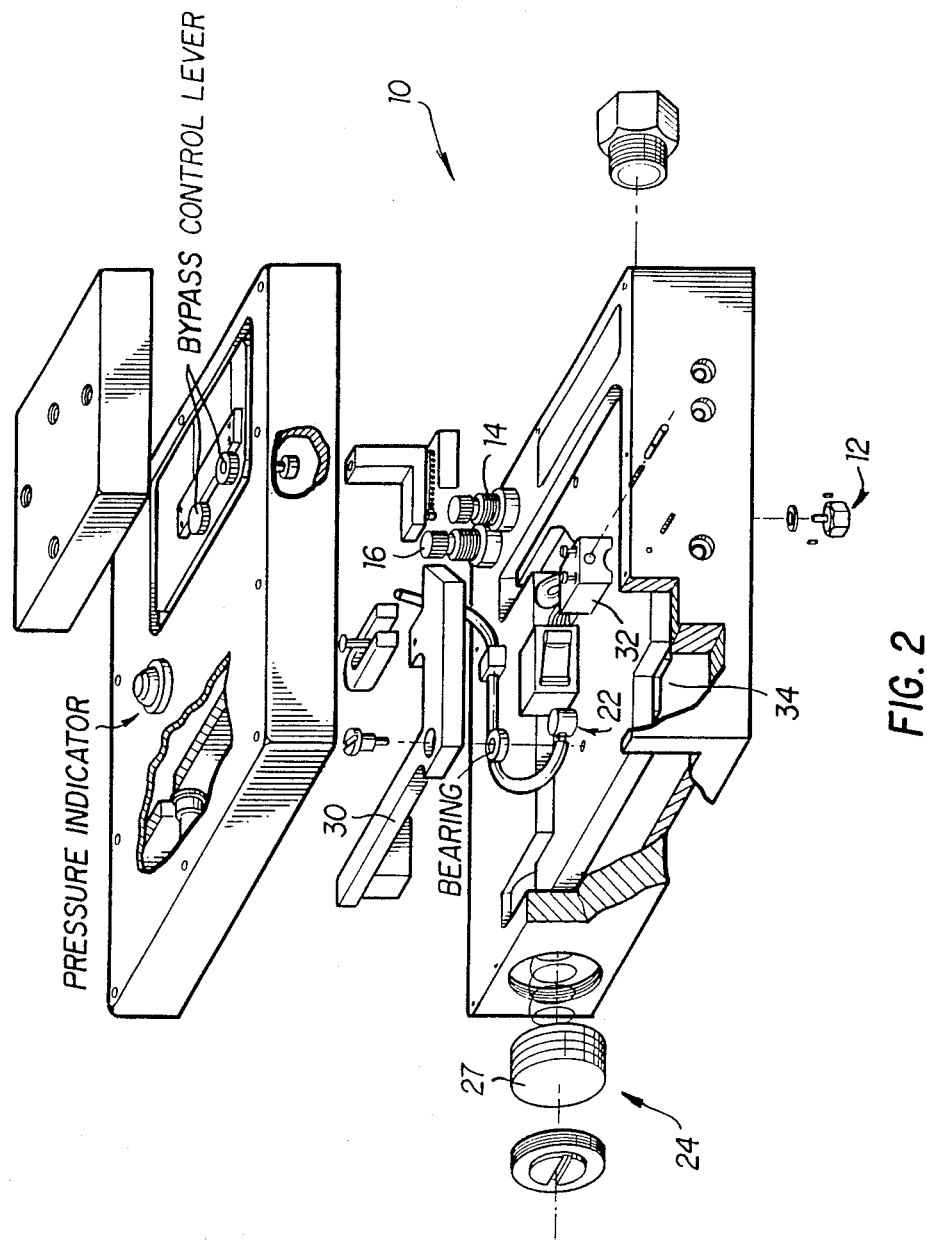
FIG. 2 is an exploded viewd of a purge module of the present invention.

Referring to FIG. 1, a schematic of the present invention is shown. FIG. 2 is an exploded view of a purge module which embodies the present invention. Like numbers correspond to like elements in FIGS. 1 and 2.

The present invention is a device for purging an enclosure 11 of harmful gases or the like. In order to purge the enclosure 11 in which equipment such as the components described by the Landa et al. patent is housed of such gases, an inert gas must flush the enclosure, thereby ridding the enclosure of such harmful gases. To accomplish the purge, a purge module 10 is mounted onto an instrument enclosure.

Gas enters the purge module via inlet port 12. In a preferred embodiment of the invention, an inert gas is used, although it is conceivable that there may be applications in which a neutralizing gas or the like could be used to practice the invention. The inert gas passes into inlet port 12.

The flow stream 13 is bifurcated and gas passes through a first regulator 14 and a second regulator 16. the first and second regulators 14, 16 are connected in parallel. In a preferred embodiment of the invention, the gas passing through the inlet port 12 is at a high pressure such as 50.0 psig and the flow downstram of the first regulator 14 is at a high pressure, such as 35.0 psig. In contrast, the gas passing through the second regulator 16 is controlled at a low pressure, such as about 0.1 psig. The gas passing through the second regulator 16 supplies gas directly to the enclosure 11. Gas is supplied to the enclosure 11 either at a high flow rate or a low flow rate, as will be described in detail hereinbelow.

Gas passing through the first regulator 14 is supplied to a cylinder 24 through a flow regulator 18 and an electrically activated directional control valve 22. When the valve 22 is in an open position, gas is allowed to flow into the purge atmosphere via gas stream 23. When valve 22 is in a closed position, inert gas is directed to the cylinder 24 via stream 25. The pressure at stream 25 is about 5.0 psig. The gas flowing into cylinder 24 moves a piston 27 which acts against spring 26. The motion of the piston 27 is timed so that the enclosure 11 has exchanged a predetermined amount, such as at least seven volumes of gas, from gas entering the enclosure 11 through the second regulator 16, before the piston closes a switch 28, as schematically illustrated in FIG. 1.

After a predetermined time has passed, the switch 28 is activated, thus providing power from power source 29 to the electrical system which is associated with the enclosure. FIG. 1 does not illustrate any particular electrical system, since the purge module may be used on a number of different devices.

The piston 27 also mechanically activates a lever 30 which when activated will change second valve 32 from an open position 33 which provides a high flow rate to the enclosure to a second position 35. When the second valve 32 is in the second position, a low flow rate of gas is introduced into enclosure 11. Thus, the low flow rate of gas is supplied to the enclosure 11 at substantially the same time as power is provided to the equipment contained in the enclosure.

The mechanism by which the first valve 22 is moved from an open position to a closed position is by means of a sensor 34. This sensor is in fluid communication with the interior of enclosure 11. When a predetermined pressure within enclosure 11 is exceeded, a circuit is closed, thereby providing power to the first valve 22. It should be noted however, that devices other than an electro-mechanical as above-described may be used to close valve 22. For example, a mechanical device such as a pnuematically actuated relief valve could be used to accomplish the same end. This pressure is a result of the purge gas entering the enclosure 11 and creating a positive feedback pressure. When power is provided to valve 22 closes and the gas stream is in communication with cylinder 24.

In operation, an inert gas under a pressure of about 50 psig is introduced into a port 12 on the purge module. The pressure is regulated by two separated pressure regulators 14, 16, each of which is preset to a required pressure setting. Regulator 14 supplies gas to a cylinder through a flow regulator 18 and an electrically activated directional control valve 22.

Second regulator 16 supplied free flowing gas under a low pressure of about 0.1 psig into a mechanically actuated directional control valve, the second valve 32, which supplies gas to the enclosure 11. A pressure sensor 31 connected to 120 volts of AC current senses the enclosure build up pressure. When a certain preset pressure or threshold is crossed, the first valve 22 is electrically actuated.

When gas is applied into the inlet port 12, the first valve 22 is open to the purge environment. Second valve 32 is mechanically forced open by a spring so that it supplies the enclosure 11 with pressurized gas at a fast flow rate, such as five cubic feet per minute.

When the enclosure 11 reaches a certain minimum pressure, the sensor 34 is actuated and produces a current which activates first valve 22 to close. All the gas into valve 22 is now directed into the cylinder 24 to control the motion of piston 27 which acts against a spring 26. The motion of the piston 27 is timed so that the enclosure 11 has exchanged at least seven volumes of gas. Although the amount of seven volumes of gas is preferred, it may be possible to exchange fewer volumes of gas without varying from the spirit of the invention. The number of volumes of gas which should be displaces depends in large part on the emvironment in which the device is being used.

At the end of travel of the piston 27, a mechanical lever 30 is actuated to supply gas at a controlled slow rate of approximately one cubic foot per minute into the enclosure 11, while microswitch 28 activates the instrument.

Should the integrity of the instrument be violated, the switch 34 will deactivate the unit immediately. Similarly, the unit will be deactivated if the input gas is lost or removed. In this way, an appropriate interlock is maintained at all times to meet standards necessary for adequate purge.

Means for overriding the above-described apparatus and method may also be provided on the purge module in order to allow a manual purge.

In a preferred embodiment of the invention, the purge module is made to attach directly to the side of the piece of equipment being purged.

In a prefered embodiment of the invention, there are two distinct lines. One line is used to supply gas at a high flow rate during the high purge cycle and the second line supplies gas at a low flow rate during the low purge cycle. Because two distinct lies are used, selective area purging is possible during the high purge cycle. During the high purge cycle, when the inert gas is flowing at a high flow rate into enclosure 11, the flow of gas can be routed to inaccessible areas of enclosure 11. In fact, during operation of electro-optical equipment of the type disclosed in the landa et al patent, there may be components in which is undesirable to have any gas flow during operation of the equipment. These area may be selectively purged during the high purge cycle and can be isolated from flow during low purge.

The foregoing description of the preferred embodiments of the invention has been presented for purposes of illustration and description. It is not intended to be exhaustive or to limit to the precise form disclosed. Obviously, many modifications and variations may be made in light of the above teachings. For example, a timing switch other than the above-described piston arrangement may be used without altering the inventive concept.

The embodiments wre chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A purge control module, comprisisng:
(a) a power source;
(b) a fluid inlet;
(c) a high pressure regulator downstream from said fluid inlet;
(d) a low pressure regulator downstream of said fluid inlet and in parallel with said high pressure regulator;
(e) a first valve downstream of said high pressure regulator, said first valve having an open position and a closed position;
(f) a switch;
(g) a means for activating said switch, said means for activating said switch being in fluid communication with said high pressure regulator when said first valve is in a closed position;
(h) a second valve downstream of said low pressure regulator, said second valve having a first position in which fluid passing through said second regulator passes through said second valve and into an enclosure at a first flow rate, and a second position in which fluid passing through said second regulator passes through said second valve and into the enclosure at a second flow rate;
(i) means for moving said second valve to said second position upon activation of said switch;
(j) a sensor, said sensor being effective to determine whether pressure within the enclosure has exceeded a predetermined level, wherein if a predetermined pressure has been exceeded, said first valve is changed to a closed position, thereby allowing fluid to be in communication with said means to activate the switch, wherein said switch is activated, power from said power source is supplied to said enclosure.

2. The purge control module of claim, wherein said means for activating the switch comprises a piston.

3. The purge control module of claim 2, wherein said piston ativates said switch a predetermined time after said first valve is in a closed position.

4. The purge control module of claim 3, wherein the predetermined time is sufficiently long to allow a volume of fluid of approximately seven times the volume of the enclosure to be passed into the enclosure by said second valve before said second valve is moved from said first position of said second valve to said second position of said second valve.

5. The purge control module of claim 4, wherein said first position of said second valve allows fluid to flow into said enclosure at a higher flow rate than said second position.

6. The purge control module of claim 5, wherein said first position of said second valve allow fluid into the enclosure at a rate of approximately five cubic feet per minutes.

7. The purge control module of claim 6, wherein said second position of said second valve allows fluid flow into the enclosure at a rate of approximately one cubic foot per minute.

8. The purge control module of claim 1, further comprising a flow regulator downstream of said high pressure regulator.

9. The purge control module of claim 1, wherein fluid is supplied through said fluid inlet at a pressure of approximately 50 psig.

10. The purge control module of claim 2, wherein said fluid is an inert gas.

11. The purge control module of claim 1, wherein said switch is a microswitch.

* * * * *